(12) United States Patent
Zabudkin et al.

US008357785B2

(10) Patent No.: US 8,357,785 B2
(45) Date of Patent: Jan. 22, 2013

(54) METHOD OF ARALKYLATION OF 4'-HYDROXYL GROUP OF ANTHRACYLINS

(75) Inventors: Alexander F. Zabudkin, Donetsk (UA); Victor Matvienko, Donetsk (UA); Alexey Matveev, Donetsk (UA); Aleksandr M. Itkin, San Diego, CA (US)

(73) Assignee: Solux Corporation, San Diego, CA (US)

( * ) Notice: Subject to any disclaimer, the term of this patent is extended or adjusted under 35 U.S.C. 154(b) by 571 days.

(21) Appl. No.: 12/126,733

(22) Filed: May 23, 2008

(65) Prior Publication Data

US 2009/0176974 A1   Jul. 9, 2009

Related U.S. Application Data

(60) Provisional application No. 61/019,770, filed on Jan. 8, 2008.

(51) Int. Cl.
 *C07G 3/00* (2006.01)
 *C07H 17/00* (2006.01)
 *C07H 15/24* (2006.01)
 *A01N 43/04* (2006.01)
 *A61K 31/70* (2006.01)

(52) U.S. Cl. .......................... 536/18.5; 536/6.4; 514/34

(58) Field of Classification Search .................... None
 See application file for complete search history.

(56) References Cited

U.S. PATENT DOCUMENTS

| | | |
|---|---|---|
| 3,803,124 A | 4/1974 | Arcamone |
| 3,963,760 A | 6/1976 | Bernardi et al. |
| 4,012,284 A | 3/1977 | Di Marco et al. |
| 4,112,076 A | 9/1978 | Arcamone et al. |
| 4,154,745 A | 5/1979 | Kende et al. |
| 4,161,480 A | 7/1979 | Pappo et al. |
| 4,188,377 A | 2/1980 | Suarato et al. |
| 4,211,864 A | 7/1980 | Vicario et al. |
| 4,225,589 A | 9/1980 | Ducep et al. |
| 4,298,535 A | 11/1981 | Vogel et al. |
| 4,345,068 A | 8/1982 | Suarato et al. |
| 4,448,724 A | 5/1984 | Cava et al. |
| 4,471,052 A | 9/1984 | Mitscher et al. |
| 4,489,206 A | 12/1984 | Cava et al. |
| 4,496,485 A | 1/1985 | Garland |
| 4,564,674 A | 1/1986 | Terashima et al. |
| 4,697,005 A | 9/1987 | Swenton et al. |
| 4,861,870 A | 8/1989 | Oppico |
| 4,973,674 A | 11/1990 | Brasca et al. |
| 4,985,548 A | 1/1991 | Caruso et al. |
| 5,091,373 A | 2/1992 | Gatti et al. |
| 5,103,029 A | 4/1992 | Cabri et al. |
| 5,130,029 A | 7/1992 | Suutarinen |
| 5,162,512 A | 11/1992 | King et al. |
| 5,180,758 A | 1/1993 | Cabri et al. |
| 5,218,130 A | 6/1993 | Cabri et al. |
| 5,510,469 A | 4/1996 | Faiardi et al. |
| 5,587,495 A | 12/1996 | Cabri et al. |
| 5,625,043 A | 4/1997 | Priebe et al. |
| 5,731,313 A | 3/1998 | Suarato et al. |
| 5,776,458 A | 7/1998 | Angelucci et al. |
| 5,814,608 A | 9/1998 | Animati et al. |
| 5,874,412 A | 2/1999 | Priebe et al. |
| 5,874,550 A | 2/1999 | van der Rijst et al. |
| 5,945,518 A | 8/1999 | Bigatti et al. |
| 5,985,887 A | 11/1999 | Caruso et al. |
| 5,998,615 A | 12/1999 | Suarato et al. |
| 6,087,340 A | 7/2000 | Gatti et al. |
| 6,096,200 A | 8/2000 | Bennett |
| 6,096,888 A | 8/2000 | Suarato et al. |
| 6,194,422 B1 | 2/2001 | Caruso et al. |
| 6,218,519 B1 | 4/2001 | Kenten et al. |
| 6,376,469 B1 | 4/2002 | Shimago et al. |
| 6,512,101 B1 | 1/2003 | King et al. |
| 6,653,455 B1 | 11/2003 | Johdo et al. |
| 6,673,907 B2 | 1/2004 | Priebe et al. |
| 7,053,191 B2 | 5/2006 | Zabudkin et al. |
| 2007/0037758 A1 | 2/2007 | Priebe et al. |

FOREIGN PATENT DOCUMENTS

| | | |
|---|---|---|
| EP | 0 014 425 A1 | 8/1980 |
| EP | 0 253 654 A2 | 1/1988 |
| EP | 0328399 A2 | 8/1989 |
| EP | 0335369 A2 | 10/1989 |
| EP | 0436474 A1 | 7/1991 |
| IT | 1196154 | 11/1988 |
| JP | 2002-255888 A | 11/2002 |
| UA | 50928 A | 11/2002 |
| WO | WO86/00073 A1 | 1/1986 |
| WO | WO96/29335 A1 | 9/1996 |
| WO | WO01/25179 A1 | 4/2001 |
| WO | WO01/87814 A2 | 11/2001 |
| WO | WO 2007/076345 A2 | 7/2007 |

OTHER PUBLICATIONS

PCT International Preliminary Report on Patentability (Chapter I of the Patent Cooperation Treaty) for PCT/US2008/086088, Applicant Solux Corporation et al., Form PCT/IB/326 and 373, SOL-109PC, Jul. 22, 2010, (5pgs).
PCT International Search Report for PCT/US2004/20679, Applicant: Solux Corporation, Form PCT/ISA220, dated May 4, 2006. (5 pages).
PCT Written Opinion for PCT/US2004/20679, Applicant: Solux Corporation, Form PCT/ISA/237, dated May 4, 2006 (4pages).
Y. Kimura, et al., Trimethylsilyl Trifluoromethanesulfonate as an Excellent Gludosidation Reagent for Antracycline Synthesis. Simple and Efficient Synthesis of Optically Pure 4-Demethroxydaunorubicin, Terashima. Chem. Letters, 1984, pp. 501-504.

(Continued)

*Primary Examiner* — Layla Bland
(74) *Attorney, Agent, or Firm* — Vista IP Law Group LLP

(57) ABSTRACT

A method for the aralkylation of anthracyclins by utilizing an aralkylating agent $R_3$—$CH_2X$ (for example, BnBr) in accordance with the reaction pathway describe by the scheme shown in FIG. 1. The present invention recognizes that 4-$R_1$, 3'-$N_3$-Daunomycines are suitable substrates for selective 4'-O-benzylation, yielding 4-$R_1$, 3'-$N_3$-4'-O-Aralkyl-Daunorubicines (in particular, 4'-O-Bn-Daunomycines). Thus, the present invention provides a pathway for a simple production of 4'-O-aralkylated derivatives of anthracyclines which can be effectively used to produce anthracyclines.

13 Claims, 1 Drawing Sheet

OTHER PUBLICATIONS

PCT International Search Report for PCT/US2006/07987, Applicant: Solux Corporation, Form PCT/ISA/220, dated Jul. 28, 2006 (4 pages).

PCT International Search Report for PCT/US2006/61978, Applicant: Solux Corporation, Form PCT/ISA?210 and 220, dated Jan. 10, 2008. (4 pages).

PCT Written Opinion for PCT/US2006/61978, Applicant: Solux Corporation, Form PCT/ISA/237, dated Jan. 10, 2008 (4 pages).

PCT Written Opinion for PCT/US2006/07987, Applicant: Solux Corporation, Form PCT/ISA/237, dated Jul. 28, 2006 (4 pages).

Office Action dated Jun. 13, 2006 for related U.S. Appl. No. 10/877,221, filed Jun. 25, 2004, Inventor: Victor Matvienko (7 pages).

Amendment dated Sep. 13, 2006 for related U.S. Appl. No. 10/877,221, filed Jun. 25, 2004, Inventor: Victor Matvienko (9 pages).

Office Action dated Oct. 24, 2006 for related U.S. Appl. No. 10/877,221, filed Jun. 25, 2004, Inventor: Victor Matvienko (7 pages).

Amendment dated Jan. 23, 2007 for related U.S. Appl. No. 10/877,221, filed Jun. 25, 2004, Inventor: Victor Matvienko (9 pages).

Office Action dated Mar. 16, 2007 for related U.S. Appl. No. 10/877,221, filed Jun. 25, 2004, Inventor: Victor Matvienko (6 pages).

Amendment dated Sep. 17, 2007 for related U.S. Appl. No. 10/877,221, filed Jun. 25, 2004, Inventor: Victor Matvienko (11 pages).

Declaration of Philipp Allexander Titulsi under 37 C.F.R. 1.132 dated Sep. 13, 2007, for related U.S. Appl. No. 10/877,221, filed Jun. 25, 2004, Inventor: Victor Matvienko (3 pages).

Declaration of Anil Dhedia under 37 C.F.R. 1.132 dated Sep. 13, 2007, for related U.S. Appl. No. 10/877,221, filed Jun. 25, 2004, Inventor: Victor Matvienko (2 pages).

Declaration of Dr. Waldemar Priebe under 37 C.F.R. 1.132 dated Sep. 15, 2007, for related U.S. Appl. No. 10/877,221, filed Jun. 25, 2004, Inventor: Victor Matvienko (38 pages).

Office Action dated Nov. 6, 2007 for related U.S. Appl. No. 10/877,221, filed Jun. 25, 2004, Inventor: Victor Matvienko (6 pages).

Office Action dated Dec. 11, 2007 for related U.S. Appl. No. 10/877,221, filed Jun. 25, 2004, Inventor: Victor Matvienko (4 pages).

Office Action dated Jun. 1, 2007 for related U.S. Appl. No. 11/367,742, filed Mar. 4, 2006, Inventor: Victor Matvienko( 8 pages).

Amendment dated Dec. 3, 2007 for related U.S. Appl. No. 11/367,742, filed Mar. 4, 2006, Inventor: Victor Matvienko (10 pages).

Notice of Allowance dated Feb. 8, 2008 for related U.S. Appl. No. 11/367,742, filed Mar. 4, 2006, Inventor: Victor Matvienko (8 pages).

PCT International Search Report for PCT/US2006/62286, Applicant: Solux Corporation et al., Forms PCT/ISA/220 and 210, dated Sep. 24, 2007 (3 pages).

PCT Written Opinion for PCT/US2006/62286, Applcant: Solux Corporation et al., Forms PCT/ISA/237 , dated Sep. 24, 2007 (5 pages).

PCT International Preliminary Report on Patentability for PCT/US2006/62286, Applicant: Solux Corporation et al., Forms PCT/ID/326, 373 and PCT/ISA/237, dated Jul. 3, 2008 (7 pages).

PCT International Preliminary Report on Patentability for PCT/US2006/061978, Applicant: Solux Corporation et al., Forms PCT/IB/326, 373 and PCT/ISA/237, dated Jun. 26, 2008 (5 pages).

Amendment and Respondse dated Feb. 21, 2008 for U.S. Appl. No. 10/877,221, filed Jun. 25, 2004, Inventor: Victor Matvienko (10 pages).

Office Action date Jun. 9, 2008 for U.S. Appl. No. 10/877,221, filed Jun. 25, 2004, inventor: Victor Matvienko (5 pages).

Amendment After Final dated Aug. 1, 2008 for U.S. Appl. No. 10/877,221, filed Jun. 25, 2004, Inventor: Victor Matvienko (7 pages).

Notice of Allowance dated Aug. 20, 2008 and Supplemental Notice of Allowability dated Oct. 31, 2008 for U.S. Appl. No. 10/877,221, filed Jun. 25, 2004, Inventor: Victor Matvienko (10 pages).

PCT International Search Report for PCT/US08/86088, Applicant: Solux Corporation, Form PCT/ISA/210 and 220, dated Jan. 26, 2009 (4 pages).

PCT Written Opinion of the International Search Authority for PCT/US08/86088, Applicant: Solux Corporation, Form PCT/ISA/237, dated Jan. 26, 2009 (3 pages).

Comprehensive Organic Chemistry. "Amines and Related Compounds." vol. 2, Nitrogen Compounds, p. 100 (1 page), 1979.

Zhang, G., Fang, L. et al."Syntheses and Biological Activities of 3'-Azido Disaccharide Analogues of Daunorubicin against Drug-Resistant Leukemia." Journal of Medicinal Chemistry 2006 vol. 49, No. 5, pp. 1792-1799 (8 pages).

Declaration Patent for an Invention in UA 50928A, Applicant: Scientific Production Company "Synbias Pharma" (1page) including issued patent UA 50928A (10pages).

The Structure of Carminomycin I, Journal of the Americal Chemical Society, 97:25, Dec. 10, 1975.

Chrisman, W. et al., The Effect of Different Amine Bases in the Swern Oxidation of B-Amino Alcohol+, Tetrahedron Letters, vol. 38, No. 12, pp. 2053-2056, 1997.

Complaint for Declaration Judgment filed in the United States District Court Southern District of California on Dec. 28, 2011, Plaintiff, *Synbias Pharma* vs. Defendant, *Solux Corporation* (19pages).

Declaration Patent for an Invention in UA 50928A, Applicant: Scientific Production Company "Synbias Pharma" (1page) including issued patent UA 50928A (10pages), 2002.

PCT International Preliminary Report on Patentability (Chapter I of the Patent Cooperation Treaty) for PCT/US2006/007987, Applicant: Solux Corporation et al., Form PCT/IB/326 and 373, dated Sep. 20, 2007 (6pages).

Extended European Search Report dated Jul. 14, 2010 in European Patent Application No. 06748302.4-2123/2187891, Applicant: Solux Corporation (5pages).

Rodygin, M. Yu, et al., Selective Monobromination of Ketones by Bis(Dimethylacetamide)Hydrogen Tribromide, 6064 Russian Journal of Organic Chemistry 30 (1994) June, No. 6, Part 1, New York, US; L.M. Litvinenko Institute of Physical Organic Chemistry and Coal Chemistry, National Academy of Sciences of Ukraine, Donetsk. Translated from Zhumal Organicheskoi Khimii, vol. 30, No. 6, pp. 827-832, Jun. 1994. Original article submitted Apr. 27, 1994.

Observations by Third Parties Pursuant to Article 115 EPC in European Application No. EP 06 748 302.4, Publication No. EP 2 187 891 A1, Applicant: Solux Corporation (4pages).

Office Communication dated May 25, 2011 in European Patent Application No. 06 748 302.4-2123, Applicant: Solux Corporation (6pages).

Response to Office Communication dated Oct. 4, 2011 in European Patent Application No. 06 748 302.4-2123, Applicant: Solux Corporation (9pages).

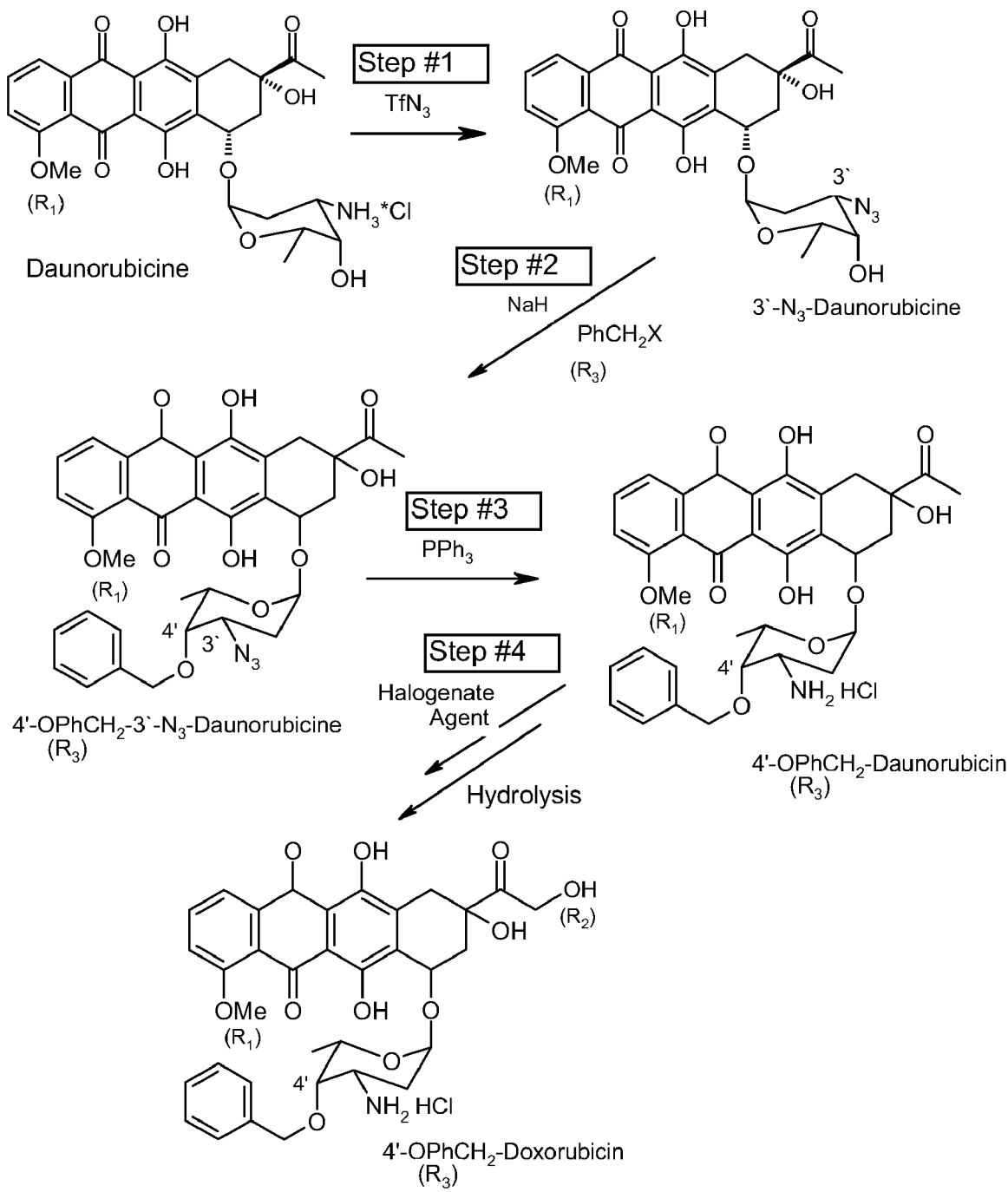

METHOD OF ARALKYLATION OF 4'-HYDROXYL GROUP OF ANTHRACYLINS

RELATED APPLICATIONS

This application claims the benefit of U.S. provisional Application No. 61/019,770, filed on Jan. 8, 2008, in accordance with 35 U.S.C. Section 119(e), and any other applicable laws. U.S. provisional Application No. 61/019,770 is hereby incorporated by reference in its entirety as if set forth fully herein.

FIELD OF THE INVENTION

The field of the invention generally relates to chemical methods used to produce anthracyclines. More specifically, the field of the invention relates to the methods and processes used to produce anthracyclines of Formula (1):

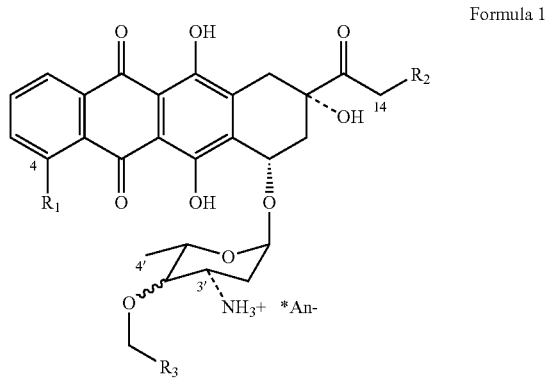

Formula 1 wherein $R_1$=H, OH, OMe; $R_2$=H, OH, OCOAlk1; Alk1=linear or branch alkyl, alkenyl or alkynyl $C_1$-$C_{12}$, 4-OCH$_2$—$R_3$ eq[uatorial] or ax[ial]; $R_3$=H, Alk1, Ar

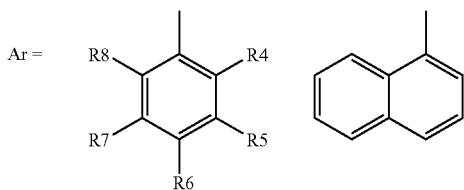

R4-R8 = substituent = linear or branch alkyl, alkenyl, alkynyl ($C_1$-$C_5$), F, Cl, CF$_3$.

An⁻—anion of a strong acid
and more specifically (4-$R_1$=OMe, 14-$R_2$=OH, ax[ial] 4'-BnO)

BACKGROUND OF THE INVENTION

Anthracyclines form one of the largest families of naturally occurring bioactive compounds. Several members of this family have shown to be clinically effective anti-neoplastic agents. These include, for example, daunorubicin, doxorubicin, idarubicin, epirubicin, pirarubicin, zorubicin, aclarubicin, and caminomycin. For instance, these compounds have shown to be useful in the treatment of breast carcinoma, acute lymphocytic and non-lymphocytic leukemia, chronic lymphocytic leukemia, non-Hodgkin's lymphoma, and other solid cancerous tumors.

However, in many cases, the problem of a transmembrane transport, or a transport across the blood-brain barrier, is of a paramount significance in improving bioavailability of a drug. The search for new anthracycline derivatives, especially for such substances that easily cross the blood-brain barrier, continues to this day. Such properties will allow widening anthracycline indications to include both primary and metastatic tumors of the central nervous system. These are some of the reasons why there is a continuously heightened interest in a synthesis of novel anthracycline antibiotics with variable lipophilicity, such as that described in U.S. Pat. Nos. 5,625,043 and 6,673,907. A change in lipophilic property may be achieved by modification of the glycoside moiety of the molecule; in particular, by alkylation of 3'-N and/or 4'-O atoms of the sugar.

In the method disclosed in U.S. Pat. No. 6,673,907, a number of compounds substituted at 3'-N are derived by direct alkylation of anthracyclines in DMF with benzylbromides. Substitution of anthracyclines at 4'-O position by aralkyl groups (substituted benzyl radicals) has traditionally been thought of as significantly less accessible. Such synthesis is complicated by the following difficulties:

(a) functional groups of both aglycone and sugar must be protected by the protection groups;

(b) production of 3'-azido-glycoside moiety is complicated by creation of equatorial and axial isomers, which further must be separated by stereospecific hydrolysis;

(c) the coupling step requires utilization of a minimum double excess amount of a sugar synthon that is produced, in its turn, in 5-6 synthetic stages. Coupling reaction completes with less than 100% stereospecificity, resulting in a creation of an undesirable stereoisomer that must be further removed;

(d) a total number of synthetic stages and chromatographic purification steps is greater than 10, precluding high yield of the desired product.

Current views on the relative reactive strength of nucleophilic groups place them in the following order: $NH_2 \geqq$ aromatic OH $\geqq$ aliphatic OH, and exclude the possibility of selective alkylation of aliphatic OH on a background of unprotected $NH_2$ or aromatic OH. This results in the complicated method of synthesis of anthracycline derivatives substituted at 4'-O position as discussed above.

Benzylation of a sugar at the 4' position in daunorubicin or its analogs by utilizing generally accepted benzylating agents such as benzyl halides+NaH; +BuLi; +t-BuOK, is impossible, because of direct preferential benzylation of nitrogen in the absence of the protective group at 3'-$NH_2$ or a generation of the reaction center at the 3'-N Prot nitrogen. In addition, benzylation of a sugar at the 4' position hinders removal of the protection group from the 3'-NH group.

The combination of these factors leads to reactions carried out simultaneously in several pathways, resulting in a poorly separable mixture of multiple products.

Previously, well-accepted methods of alkylation of 4' hydroxyl group of sugar utilized 3,4-di-O-Acetyl-Rhamnal as a starting material. It was first converted to 3-azide (racemate); then, the desired optical isomer was separated and benzylated with BnBr in the presence of NaH. The synthon created by such method was then coupled to an independently-synthesized aglycone. Further modifications and removal of the protection groups yielded the desired final product.

Simplification in production of this class of compounds by modification of the microbiologically produced anthracycline precursors without separation of aglycone and sugar confers a great advantage to such process. For example, one such approach to the synthesis of idarubicin is described in U.S. Pat. No. 7,053,191. The process described in U.S. Pat. No. 7,053,191 decreases the number of synthetic stages from 11 or 12 to just 5.

A method of modifying the 3'-$NH_2$ to 3'-$N_3$ group in a glycoside part of the anthracycline molecule was previously described in the Journal of Medicinal Chemistry 2006 Vol 49, No 5, pp 1792-1799. This method allows production of a corresponding azide while keeping the anthracycline molecule intact.

SUMMARY OF THE INVENTION

The present invention is directed to an innovative method for the aralkylation of anthracycline by utilizing an aralkylating agent $R_3$-$CH_2X$ (for example, BnBr) in accordance with the reaction pathway describe by the scheme shown in FIG. 1. The present invention recognizes that 4-$R_1$, 3'-$N_3$-Daunomycines are suitable substrates for selective 4'-O-benzylation, yielding 4-$R_1$, 3'-$N_3$-4'-O-Aralkyl-Daunorubicines (in particular, 4'-O-Bn-Daunomycines). Thus, the present invention provides a pathway for a simple production of 4'-O-aralkylated derivatives of anthracyclines.

BRIEF DESCRIPTION OF THE DRAWINGS

FIG. 1 is a schematic view of a reaction pathway according to one embodiment of the present invention.

DETAILED DESCRIPTION OF THE INVENTION

The method for the aralkylation of anthracyclins by utilizing an aralkylating agent $R_3$—$CH_2X$ (for example, BnBr) according to the present invention comprises the reaction steps as shown in FIG. 1, which can be described as follows. The starting material is an anthracycline derivative salt in alcohol (preferably methanol). A solution of $TfN_3$ in dichloromethane is added to the solution of anthracycline derivative salt in alcohol (preferably in methanol), and the mixture is incubated for 4-24 hours, until the starting material has completely reacted. This results in the azide derivative represented by Formula 3:

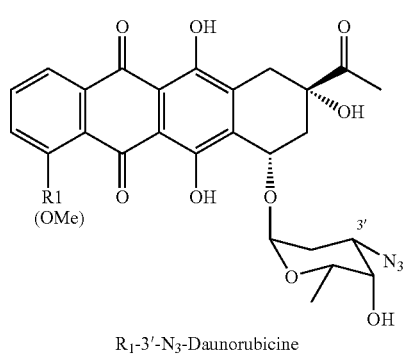

$R_1$-3'-$N_3$-Daunorubicine

Formula 3

The azide derivative represented by Formula 3 is dissolved in an aprotic solvent which is stable to the action of strong bases and alkylating agents such as dialkylamides, simple ethers (linear ethers (ex. Diethylether, methyl-t-butyl ether), cyclic ethers (ex. THF), and glyme ethers) or mixtures of such solvents (preferably DMF). While stirring, an excess of a strong base (preferably NaH), in a ratio of 1.2-10 M to 1 M of anthracycline, is added to the mixture. Then, an alkylating agent $R_3CH_2X$ (for example BnBr) is added in an excess ratio of 1.2-10 M to 1 M of anthracycline at a temperature from 0 to 90° C. or at a boiling point of the solvent. The duration of the reaction greatly depends on the reactivity of the alkylating agent and can vary from hours to days. The completion of the reaction is monitored by thin-layer chromatography ("TLC").

After completion of the reaction, the reaction mixture is evaporated under sub-atmospheric pressure conditions and washed with diethyl ether. The product is extracted by dichloromethane from the organic-aqueous emulsion of the reaction mixture in distilled water. The dichloromethane extract is washed with distilled water, and the dichloromethane is then removed by evaporation at low pressure.

The resulting alkylated anthracycline azide is dissolved in THF, and 2 M excess of triphenylphosphine is added to the solution. The duration of this reaction varies from hours to days. Again, the completion of the reaction is monitored by TLC. This results in the aralkylated anthracycline represented by Formula 4:

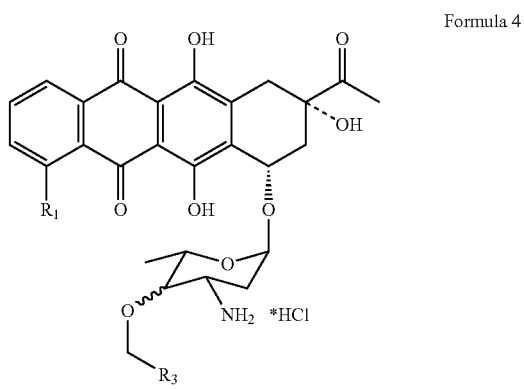

Formula 4

The aralkylated anthracycline represented by Formula 4 is further halogenized by a complex halogenide as represented by Formula 2:

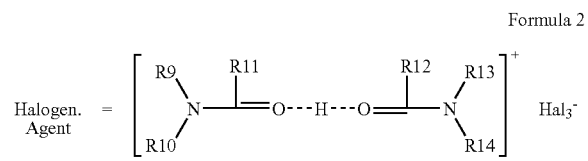

Formula 2 where $R_9$ through $R_{14}$ are defined as H or a hydrocarbon radical of 1 to 4 carbon chains ($C_1$-$C_4$); Hal is Cl, Br, I The solvents utilized for this reaction are medium-basicity aprotic solvents that are able to bind the hydrogen halide produced during halogenization, for example, amides, simple ethers and mixtures thereof, preferably dimethylformamide and tetrahydrofuran. This reaction is conducted at a temperature of 20-60° C. for 2-20 hours, preferably at 50° C. for about 3 hours. This results in a 14-halogenated derivative. This 14-halogenated derivative is then precipitated by adding cold acetone or acetonitrile and hydrolyzed in aqueous-acetone solution in the presence of carboxylic acid salts, preferably sodium formate, at a pH=2.5-5.5, or more preferably a pH=3.5-4.0. If production of 14-0 esters is desired (R2=OCOAlk1; Alk1=linear or branched alkyl, alkenyl or alkynyl $C_1$-$C_{12}$), the salt of the corresponding carboxylic acid is utilized.

Example

First, 20 g of daunorubicin hydrochloride is dissolved in 125 mL MeOH. A solution of 7.5 g of $K_2CO_3$ in 20 mL of water is added and intensely stirred for 1 minute. A solution of $TfN_3$ in dichloromethane is then added to the mixture. The mixture continues to be stirred on a magnetic stirrer until the full conversion of the original anthracycline is achieved (confirmed by TLC). The resulting reaction mass is then poured in 300 mL of water. The organic layer is separated, and water is extracted using dichloromethane. The dichloromethane is then evaporated from the solution in a rotor evaporator. This results in 3'-$N_3$-Daunomycin.

The 3'-$N_3$-Daunomycin is dissolved in 100 mL dimethylformamide, and 2 g of 60% suspension of NaH in paraffin is added. The mixture is stirred at room temperature for 30 minutes, and 4 mL of benzylbromide is then added to it. Stirring continues until the concentration of the original daunomycin azide is decreased 8-10 times. The resulting reaction mixture is then poured into acidified distilled water and extracted using dichloromethane. The dichloromethane is then evaporated from the solution in a rotor evaporator.

The resulting semisolid residue is dissolved in 100 mL tetrahydrofurane, and 7 g of triphenylphosphine is added to the solution. This solution is left at room temperature until full conversion of 3'-$N_3$-4'-OBn-Daunomycin is reached. The resulting reaction mass is fully dried by evaporation, and the excess triphenylphosphine is removed by chromatography. This results in 4'-OBn-Daunomycin The resulting 4'-OBn-Daunomycin is dissolved in 100 ml of dimethylformamide, and 5 g of hydrogen dibromobromate bis(dimethylformamide) is added to the mixture. The mixture is then incubated at 40° C. for 2 hours. Afterwards, the reaction mixture is poured into 350 mL of acetonitrile. The precipitated sediment is filtered and washed with acetonitrile and the solvent is removed.

The solid sediment is dissolved in a mixture of 80 ml of acetone, 80 ml of 0.25 M aqueous solution of hydrogen bromide, and 8 grams of sodium formate. The reaction mixture is incubated for 30 hours at 35° C.

The acetone is then removed from the reaction mixture, and the residue purified by chromatographic purification. The yield is 3.1 g of 4'-OBn-Doxorubicin.

We claim:
1. A method of producing 4'-O-aralkyl derivatives of anthracyclines of Formula 1,

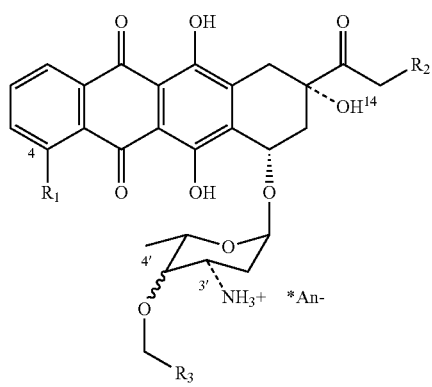

Formula 1 wherein $R_1$=H, OH, or OMe; $R_2$=H, OH, or $OCOAlk1$; Alk1=linear or branch alkyl, alkenyl or alkynyl $C_1$-$C_{12}$; 4'-$OCH_2$—$R_3$ is equatorial or axial; $R_3$=Alk1 or Ar

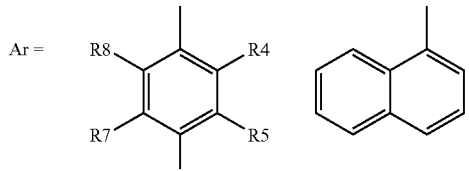

R4-R8 = H or substituent = linear or branch alkyl, alkenyl, alkynyl ($C_1$-$C_5$), F, Cl, $CF_3$.

$An^-$=anion of a strong acid; by utilizing an alkylating agent $R_3$—$CH_2X$, wherein X is selected from the group consisting of Cl—, Br—, I—, Ts, $CH_3SO_2O$—$CF_3SO_2O$, comprising the steps of:
(a) providing a starting material comprising an anthracycline derivative salt of daunorubicine hydrochloride in alcohol, according to the following formula wherein $R_1$ is defined as in Formula 1;

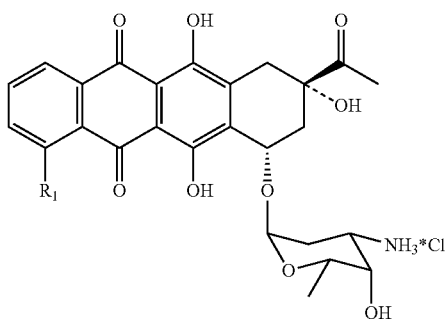

Daunorubicine (b) incubating said starting material with a solution of $TfN_3$ in dichloromethane until said starting material is completely reacted, to produce 3'-$N_3$-daunorubicine according to the following formula wherein $R_1$ is as defined in Formula 1;

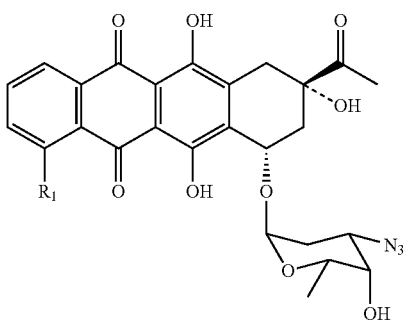

3'-$N_3$-Daunorubicine (c) dissolving the product of step (b) in an aprotic solvent;
(d) reacting the product of step (c) with an excess of an alkylating agent $R_3$—$CH_2X$ and a strong base, to produce 4'-$OR_3$—$N_3$-daunorubicine, according to the following formula, wherein $R_3$ and X are as defined in Formula 1;

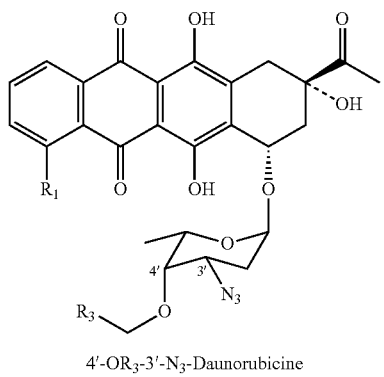

4'-OR₃-3'-N₃-Daunorubicine

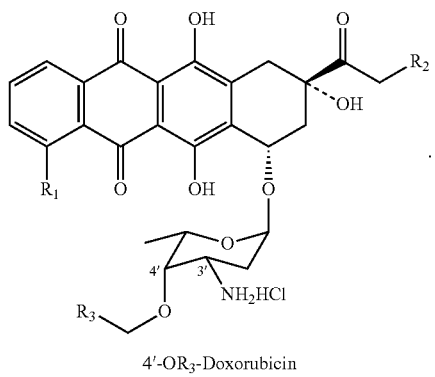

4'-OR₃-Doxorubicin (e) dissolving the product of step (d) in Tetrahydrofuran (THF) and reacting it with triphenylphosphine, to produce 4'-OR₃-daunorubicin according to the following formula wherein R₃ is as defined in Formula 1;

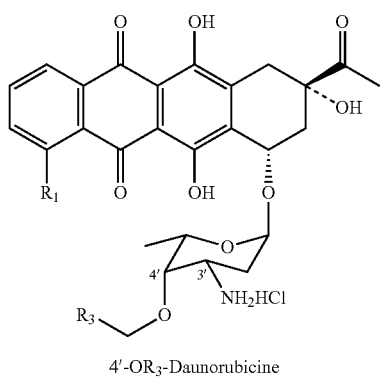

4'-OR₃-Daunorubicine (f) reacting the product of step (e) with a complex halogenide of Formula 2,

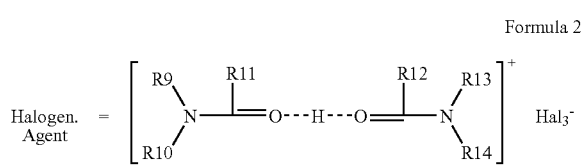

Formula 2 where R₉ through R₁₄ are defined as H or a hydrocarbon radical of 1 to 4 carbon chains (C₁-C₄); Hal is Cl, Br, I in a medium basicity aprotic solvent, to produce a 14-halogenated derivative;

(g) hydrolyzing the product of step (f), to produce 4'-OR₃-doxorubicin according to the following formula wherein R₁ and R₂ are as defined in Formula 1, 2. The method of claim 1, wherein the alkylating agent used in step (d) comprises R₃—CH₂X, wherein R₃=Ar;

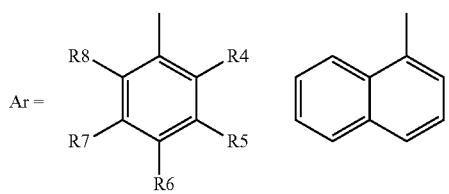

R4-R8 = H or substituent = linear or branch alkyl, alkenyl, alkynyl (C₁-C₅), F, Cl, CF₃.

and wherein the reaction of step (d) is performed with said alkylating agent utilized in the proportion of 1.2-10 M to 1 M of anthracycline, the reaction of step (d) is conducted in one of dialkylamides or ethers, and the reaction of step (d) is conducted at a temperature selected from the group consisting of 0° C. to 90° C., and the boiling point of said aprotic solvent.

3. The method of claim 2, wherein said medium basicity solvent is selected from the group consisting of amides, simple ethers and mixtures thereof, and the reaction of step (f) is conducted at a temperature of 20° C. to 60° C. for between 2 and 20 hours.

4. The method of claim 3, wherein the reaction of step (f) is conducted at a temperature of 50° C. for 3 hours.

5. The method of claim 4, wherein said medium basicity solvent is selected from the group consisting of dimethylformamide and tetrahydrofuran.

6. The method of claim 5, wherein the incubation of step (b) is performed from 4 to 24 hours, until said starting material is completely reacted.

7. The method of claim 1, wherein said aprotic solvent is selected from the group consisting of dialkylamides, simple ethers, linear ethers, cyclic ethers or mixtures thereof.

8. The method of claim 6, wherein said aprotic solvent is selected from the group consisting of THF or Dimethylformamide (DMF).

9. The method of claim 1, wherein said alkylating agent is benzylbromide.

10. The method of claim 2, wherein said alkylating agent is benzylbromide and said strong base is NaH.

11. The method of claim 8, wherein said alkylating agent is benzylbromide and said strong base is NaH.

12. The method of claim 8, wherein said alcohol is methanol.

13. The method of claim 1, wherein R₁=OMe; R₂=OH; and 4'-BnO is in an axial position.

* * * * *